United States Patent [19]

Nocito et al.

[11] Patent Number: 5,043,489

[45] Date of Patent: Aug. 27, 1991

[54] METHOD OF PREPARING MONOHALOGENATED NITROALKANES

[75] Inventors: Vincent Nocito, Buffalo Grover; Louis J. Bedell, Mount Prospect; Mathew I. Levinson, Chicago, all of Ill.

[73] Assignee: Angus Chemical Company, Northbrook, Ill.

[21] Appl. No.: 529,747

[22] Filed: May 24, 1990

Related U.S. Application Data

[63] Continuation of Ser. No. 279,526, Dec. 2, 1988, abandoned.

[51] Int. Cl.$^5$ ............................................. C07C 205/01
[52] U.S. Cl. .................................. 568/946; 568/943; 568/947; 568/948
[58] Field of Search ............. 568/943 APS, 946 APS, 568/947 APS, 948 APS

[56] References Cited

U.S. PATENT DOCUMENTS

| | | | |
|---|---|---|---|
| 1,996,388 | 4/1935 | Ramage | 568/946 |
| 2,181,411 | 11/1939 | Vanderbilt | 568/946 |
| 2,397,384 | 3/1946 | Tindall | 568/946 |
| 2,632,776 | 3/1953 | Slagh | 568/946 |
| 3,096,378 | 7/1963 | Levering | 568/946 |
| 3,106,588 | 10/1963 | Wilheim | 568/946 |
| 3,159,686 | 12/1964 | Burk et al. | 568/946 |
| 4,329,523 | 5/1982 | James et al. | 568/948 |
| 4,517,394 | 5/1985 | Wang et al. | 568/948 |

Primary Examiner—Deborah L. Kyle
Assistant Examiner—Valerie D. Fee
Attorney, Agent, or Firm—Leydig, Voit & Mayer

[57] ABSTRACT

A method of preparing a monohalogenated nitroalkane which comprises reacting equal molar quantities of an alkali metal hydroxide and a nitroalkane in a suitable medium to form a nitronate salt therein, promptly mixing the medium containing the nitronate salt with an equal molar quantity of a halogen to form a monohalogenated nitroalkane in the medium, promptly adding a material to the medium containing the monohalogenated nitroalkane to terminate any further halogenation therein, and recovering the monohalogenated nitroalkane from the medium.

7 Claims, No Drawings

METHOD OF PREPARING MONOHALOGENATED NITROALKANES

This is a continuation of copending application Ser. No. 279,529, filed on Dec. 2, 1988, now abandoned.

This invention is in the field of chemical synthesis and is directed to a method for the preparation of monohalogenated nitroalkanes substantially free of polyhalogenated nitroalkanes.

BACKGROUND OF THE INVENTION

Halogens are known to react readily with nitroalkanes. This reaction occurs with respect to the hydrogens bonded to the same carbon as the nitro group. In the presence of an alkaline catalyst, complete halogenation of the nitroalkane is easily achieved. Thus, nitromethane reacts readily to produce chloropicrin in high yield as illustrated below.

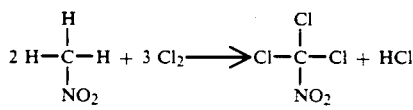

Due to the ease with which complete halogenation takes place, however, it is difficult to prepare monohalogenated nitroalkanes in high yield. This difficulty is compounded by the difficulty in separating the monohalogenated product from any polyhalogenated product formed in the halogenation reaction.

A method of preparing monochlorinated nitromethane is described in U.S. Pat. No. 2,309,806. In this process, approximately equivalent quantities of aqueous solutions of nitromethane and a basic alkali metal hydroxide are reacted to form an alkali metal salt of the nitromethane which is, in turn, reacted with gaseous chlorine at a temperature not substantially in excess of 50° C. to produce monochlorinated nitromethane. The monochlorinated nitromethane is subsequently recovered by distillation.

More recent U.S. Pat. No. 3,096,378 describes a method of preparing monochlorinated nitroethane. The described process consists of a rather rigidly controlled chlorination of nitroethane with a special emphasis being placed on the control of reaction vairiables such as agitation, temperature, and time of reaction. An aqueous solution of the sodium salt of nitroethane is prepared by adding a solution of sodium hydroxide to a slurry of nitroethane in water with cooling. Sodium chloride is added to the solution to decrease the solubility of the monochlorinated nitroethane to be formed in the aqueous solution. The solution of the sodium salt of nitroethane is then cooled to 0° C. Chlorine is bubbled through the solution while avoiding stirring, and the monochlorinated nitroethane is formed and removed from the reaction mixture.

BRIEF SUMMARY OF THE INVENTION

It is an object of the present invention to provide a method of preparing and recovering a high yield of high purity monohalogenated nitroalkane.

It is a further object of this invention to provide a means of preparing monohalogenated nitroalkanes of high purity and in high yields without the use of salt additives to control solubility or the need to avoid stirring the reaction mixture.

Yet another object of this invention is to provide a method of preparing monohalogenated nitroalkanes which employs a relatively simple recovery procedure.

A still further object of this invention is to provide a process for the preparation of monochlorinated nitroalkanes which can be operated in either a batch or a continuous process.

These and other objects and advantages of this invention, as well as additional inventive features, will become apparent from the description which follows.

Monohalogenated nitroalkanes are prepared in accordance with the present invention by reacting equal molar quantities of an alkaline material and a nitroalkane in a suitable medium to form a nitronate salt therein, immediately mixing the medium containing the nitronate salt with an equal molar quantity of a halogen to form monohalogenated nitroalkane in the medium, optionally and promptly adding a compound such as sodium bisulfite to the medium to destroy any unreacted halogen therein and thereby to terminate any further halogenation reaction, and recovering the monohalogenated nitroalkane from the medium. By alkaline material is meant an alkali metal salt or an amine. The recovery may be accomplished by distillation of a water azeotrope of the monohalogenated nitroalkane and separation of the monohalogenated nitroalkane layer from the remainder of the distillation product.

DETAILED DESCRIPTION OF THE INVENTION

While the invention will be described in connection with certain preferred embodiments, it is not intended to limit the invention to the particular embodiments. On the contrary, it is intended to cover all alternatives, modifications, and equivalent processes as may be included within the spirit and scope of the invention as defined by the appended claims.

The present invention constitutes a method of preparing monohalogenated nitrokanes of the formula:

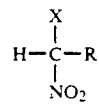

where R is hydrogen or an alkyl group and X is a halogen. The inventive method involves the reaction of a mono alkali salt of a nitroalkane, i.e., a nitronate salt, with a halogen to form the monohalogenated nitroalkane which is subsequently recovered from the reaction mixture.

The nitronate salt is prepared by reacting essentially equal molar quantities of an alkali metal hydroxide and a primary nitroalkane such as nitromethane, nitroethane or 1-nitropropane. The reaction may take place in any suitable vessel equipped with an agitator and cooling jacket or may be performed in a continuous reactor consisting of a tube containing a static mixer. The reaction takes place at temperatures below about 40° C. and when in a batch operation at low temperature, e.g., 0° C.±10° C., and preferably in an aqueous medium in which an aqueous solution of the nitroalkane is mixed with an aqueous solution of the alkali metal hydroxide, resulting in an aqueous solution of the nitronate salt. Other solvents can also be used. The preferred alkali metal hydroxide is sodium hydroxide, but other alkali metal hydroxides can be utilized in the practice of the present invention.

The nitronate salt thus formed is promptly mixed with a halogen in equal molar quantities. Again, the reaction may take place in any suitable vessel. Preferably, an aqueous nitronate salt solution is charged into a reactor containing a solution of the halogen. Cooling is supplied to maintain the vessel at temperature as recited in the preceding paragraph, with agitation. If a continuous system is desired, anhydrous halogen or a halogen solution can be fed into a tube reactor equipped with a static mixer simultaneously and in equal molar quantity with the nitronate salt solution. The process is preferably operated in an aqueous system, although other solvent systems can also be utilized. For example, if the halogen is not sufficiently water-soluble, a different, more suitable, solvent for the halogen may be used.

Immediately following formation of the monohalogenated nitroalkane, the solution is treated with a compound to destroy any unreacted halogen in the reaction mixture. The compound employed to destroy any unreacted halogen is preferably sodium bisulfite and is preferably added to the reaction mixture in the form of a saturated solution.

The resulting monohalogenated nitroalkane is recovered from the reaction mixture, preferably by distillation of a solvent azeotrope of the desired product and separation of the bottom product layer by decantation from a suitable distillation trap. The monohalogenated nitroalkane produced by this process will be on the order of 90-95% pure.

The following examples further illustrate the present invention but, of course, should not be construed as in any way limiting its scope.

EXAMPLE 1

This example illustrates the batch conversion of nitromethane to monobromonitromethane.

An aqueous nitromethane solution (10% wt/wt) was prepared from nitromethane (500 g, 98.4%, 8.06 moles) and water (4,500 g). The aqueous nitromethane solution and an aqueous sodium hydroxide solution (1,638.3 g, 20% wt/wt, 8.2 moles) were pumped into a four-neck, 500 ml, round-bottom flask equipped with a mechanical stirrer, thermometer, overflow tube, and immersed in a dry ice-acetone bath. The two streams were controlled with precision metering pumps and were contacted just prior to entering the vessel in a mixing T through which nitrogen was sparged to facilitate mixing and remove air. The rate of pumping was controlled so that nitromethane and caustic were reacted in a 1:1 molar ratio to form a nitronate salt and the net out fall from the overflow tube was 50.85 cc/min. The liquid level in the flask was controlled by raising or lowering the overflow tube so the vessel was half full. The pot temperature was maintained at $-5°$ to $0°$ C. with cooling.

The nitronate salt solution overflow from this 500 ml flask was directed through a polypropylene tube subsurface into a four-neck, 12 liter, roundbottom flask equipped with a mechanical stirrer, thermometer, and dry ice vapor trap and which was charged with water (1,000 g) and bromine (8.2 moles, 1,310.6 g). The pot temperature in the 12 liter vessel was maintained at $-5°$ to $0°$ C. by immersion in a dry ice-acetone bath.

Following completion of the nitronate salt solution addition to the bromine solution, the dark red monobromonitromethane solution was stirred for 15 minutes. A charge of saturated sodium bisulfite solution (25 cc) was then added to destroy the unreacted bromine, whereupon the reaction mixture turned colorless.

Agitation was then stopped and the entire reactor contents were transferred to a 12 liter round-bottom flask equipped with a mechanical stirrer, thermometer, and a Vigreux distillation column topped with a Dean-Stark trap and a cold water condenser.

An impure azeotropic forecut was taken (head temperature was $90°-94°$ C.) and the main product cut was collected as a 1:1 water azeotrope (head temperature=$94°-101°$ C., pot temperature=$100°-105°$ C., 760 mm Hg). The colorless lower monobromonitromethane layer was drawn off semicontinuously during the course of distillation and the upper aqueous layer was allowed to overflow back to the pot.

The product thus collected (1,088.3 g) was assayed by GLPC internal standard analysis as consisting of 90.5 wt.% monobromonitromethane, approximately 1.4 wt.% bromonitroethane, and approximately 2.4 wt.% dibromonitromethane. The conversion of nitromethane (500 g, 98.4%, 8.06 moles) to monobromonitromethane (985 g, 7.03 moles) was 87.28 mole percent.

EXAMPLE 2

This example illustrates a continuous process for the preparation of monobromonitromethane.

The reaction system consisted of a pair of static mixers, connected in series, immersed in a dry ice-acetone bath. The nitronate reactor was 0.7 meter section of Kimax process pipe (2 cm ID). The reactor contained a 21 element Teflon static mixer. The working volume of the reactor was 0.185 liter. Connecting lines to the reactor were 0.95 cm Teflon. Tubing connectors were made of either Teflon or Kynar. The nitromethane solution and sodium hydroxide were fed to the reactor using FMI Metering pumps (Model RP-B). The nitromethane pump was equipped with a #2, 316 SS pump head (0.95 cm od piston). The sodium hydroxide pump was a #2, ceramic pump head (0.95 cm od piston). The effluent from the reactor was passed to the inlet of the bromination reactor. Bromination of the nitronate solution was conducted in a second static mixer reactor. The bromination reactor was constructed of Kimax process pipe (0.5 m long, 1.25 cm ID, 51 cc volume). The reactor contained a 24 element Teflon static mixer. Anhydrous bromine was fed to the reactor by an FMI metering pump (Model RP-B) equipped with a #2 ceramic head pump. The effluent from the bromination reactor was sent to a polyethylene holding tank.

A solution of nitromethane (98 wt.%, 50 Kg) in 450 Kg of condensate water was prepared. The solution was mixed for fifteen minutes and then discharged to steel drums. A commercial solution of 50% NaOH was also employed in this process. The caustic was titrated with 1N HCl to confirm concentration.

The feed pumps for the three reactant streams were calibrated to give a 1:1:1 mole ratio of nitromethane, sodium hydroxide, and bromine. Typical flow rates for the reactants are shown below.

| Component | Volume (cc/min) | Weight (g/min) | Moles (moles/min) |
|---|---|---|---|
| nitromethane (10% Aq.) | 1013.17 | 1031.61 | 1.690 |
| sodium hydroxide (50% Aq.) | 87.82 | 134.65 | 1.683 |
| bromine | 86.10 | 271.48 | 1.699 |

-continued

| Component | Volume (cc/min) | Weight (g/min) | Moles (moles/min) |
|---|---|---|---|
| (Anhyd.) | | | |

The above flow rates led to a residence time in the nitronate reactor of 10.08 seconds. The residence time in the bromination reactor was 2.58 seconds.

The flow rates for the three reactant streams were checked against the pump calibration. The temperature of the cooling bath was lowered to 0° C. using ice water. The nitromethane and sodium hydroxide pumps were switched on simultaneously, and the bromine pump was switched on ten seconds later. The temperature of the cooling bath was adjusted to −20° to −30° C. with dry ice pellets. The temperature of the reactor outfall and the pH were monitored every five minutes. Typical outlet temperature from the bromination reactor was +42° C. The pH of the effluent was typically pH 0.1 or less. The bromonitromethane product and aqueous phase were treated with small quantities of sodium bisulfite to destroy excess bromine. These layers were also sampled and tested for nitromethane and bromonitromethane content. The layers were then azeotropically distilled to obtain the monobromonitromethane.

This continuous reactor was operated for a five day period. Typical runs were of 30 minutes or less duration. The typical assay of the product was 92–94 wt.% monobromonitromethane, 4–6 wt.% nitromethane, 1–2 wt.% dibromonitromethane, and a trace amount of tribromonitromethane.

EXAMPLE 3

This example illustrates a batch process suitable for the preparation of monobromonitroethane.

In a suitable vessel equipped with an agitator, 24 grams of nitroethane and 600 grams of water were added. The reaction mixture was cooled to 0° C., and 26 grams of 50% sodium hydroxide solution were added slowly over a five minute period. The resulting nitronate solution was fed to a solution of 52 grams of bromine and 300 grams water, which was prepared in a second round bottom flask equipped with an agitator. Addition of the nitronate solution was accomplished in seven minutes. The temperature of the reaction mixture was maintained at 0° C.±10° C. Following the addition, the resulting solution was agitated for thirty minutes and treated with 25 ml of saturated sodium bisulfite solution to remove any residual bromine.

When agitation was stopped, a Vigreux column was added to the flask along with a Dean-Stark trap and cold water condenser. A water product azeotrope was removed at 94°–101° C., and product was recovered as it separates in the Dean-Stark trap.

EXAMPLE 4

This example sets forth an illustrative procedure for the preparation of monochloronitromethane.

The apparatus used to prepare monochloronitromethane included three reactors: a nitronate reactor, a chlorination reactor, and a distillation reactor. The nitronate reactor was a 500 ml, roundbottom flask equipped with a thermometer, agitator, two feed reservoirs and pumps, and a nitrogen purge line. The chlorination reactor was a 12 liter, round-bottom flask equipped with a dry ice reflux condensor, inlets for chlorine and nitronate, an agitator, and a scrubber (10% NaOH/10% NaHSO$_3$). The distillation reactor was a 12 liter, round-bottom flask equipped with a thermometer, agitator, 1.5 feet Vigreux column, a Dean-Stark trap, and a scrubber (10% NaOH/10% NaHSO$_3$).

The following procedure was followed in preparing the monochloronitromethane. 6,100 grams of a 10 percent aqueous nitromethane (10 moles) solution was charged to the feed tank of the nitronate reactor, and 2,000 grams of a 20 percent sodium hydroxide (10 moles) solution was charged to the second feed tank of the nitronate reactor. The overflow nitronate reactor (500 ml) was charged with 150 ml of DI water and then cooled to 0° C. with a dry ice-acetone bath. The dip pipe of the nitronate reactor was adjusted to give a residence time of three minutes at a feed rate of 53.3 cc per minute. The chlorination reactor was charged with one liter of methylene chloride and then cooled to −5° C. with a dry ice-acetone bath. The agitator was then started. Chlorine was sparged into the methylene chloride until a gentle reflux of liquid chlorine was apparent in the dry ice reflux condensor. At that time, the flow of nitrogen was started to the nitronate reactor (20 cc/minute). After two minutes, the nitromethane feed pump was started (41.5 ml/minute) along with the sodium hydroxide feed pump (11.8 ml/minute). The temperature in the nitronate reactor was continuously monitored and maintained at 0°–5° C.

The flow of chlorine to the chlorination reactor was then started (feed rate: 8.5 grams/minute for the first 40 minutes, 5.95 grams/minute for the next 30 minutes, 2.55 grams/minute for the final 55 minutes). The sodium nitronate solution (yellow) overflowed continuously to the chlorination reactor, and the temperature in the chlorination reactor was maintained at 0°–5° C. A total of 760 grams of chlorine was fed to the reactor (10.7 moles) over the 2.6 hour nitronate feed period.

Upon completion of the feed addition, the nitronate pumps were stopped. The reaction mixture was allowed to warm to 25° C. and then stirred for one hour. The solution was cloudy yellow with a bright yellow organic phase at the bottom.

The entire contents of the reaction flask was transferred to the distillation reactor. The reaction mixture was heated to boiling (atmospheric pressure), and a bisulfate scrubber was used to remove chlorine evolved during the heating. A forecut was collected up to a head temperature of 91° C. The product cut was collected as the bottom layer of the azeotrope between 91°–101° C. (head; 94°–104° C. pot).

By following the foregoing procedure, 824 grams of product was recovered containing 88 wt.% monochloronitromethane, 2–3 wt.% dichloronitromethane, 1–2 wt.% trichloronitromethane, and 5–7 wt.% nitromethane. It is believed that the nitromethane in the product could have been removed from the recovered product by increasing the temperature of the forecut to 94° C.

What is claimed is:

1. A continuous method of preparing monohalogenated nitroalkanes which comprises simultaneously feeding into a static mixer approximately equal molar quantities of an alkaline material and an aqueous solution of a nitroalkane to form a nitronate salt therein, promptly feeding continuously the nitronate salt and an equal molar quantity of a halogen into a static reactor to form monohalogenated nitroalkane, promptly adding to the monohalogenated nitroalkane an aqueous solution of sodium bisulfite in an amount sufficient to terminate any further halogenation therein, and recovering the monohalogenated nitroalkane.

2. The method of claim 1 wherein the monohalogenated nitroalkane is recovered from the aqueous medium by distillation of a water azeotrope of the monohalogenated nitroalkane.

3. The method of claim 1 wherein the reaction between the alkaline material and the nitroalkane occurs at a temperature between about −10° C. and 40° C.

4. The method of claim 1 wherein the reaction between the nitronate salt and the halogen occurs at a temperature between about −10° C. and 40° C.

5. The method of claim 1 wherein the halogen is selected from the group consisting of chlorine and bromine.

6. The method of claim 5 wherein the nitroalkane is nitromethane and the monohalogenated nitroalkane is monohalonitromethane.

7. The method of claim 5, wherein the nitroalkane and the monohalogenated nitroalkane contain a lower alkyl group.

* * * * *